US00PP15263P2

(12) United States Plant Patent
Slaughter et al.

(10) Patent No.: US PP15,263 P2
(45) Date of Patent: Oct. 26, 2004

(54) PEACH TREE, 'BURPEACHNINETEEN'

(50) Latin Name: *Prunus persica*
Varietal Denomination: Burpeachnineteen

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 1 day.

(21) Appl. No.: 10/734,488

(22) Filed: Dec. 11, 2003

(51) Int. Cl.[7] ..... A01H 5/00
(52) U.S. Cl. ..... Plt./197
(58) Field of Search ..... Plt./197

*Primary Examiner*—Anne Marie Grunberg
*Assistant Examiner*—S B McCormick-Ewoldt
(74) *Attorney, Agent, or Firm*—Wells St. John P.S.

(57) ABSTRACT

A new and distinct variety of peach tree (*Prunus persica*), denominated varietally as 'Burpeachnineteen', and which produces an attractively colored yellow-fleshed, clingstone peach which is mature for harvesting approximately May 8th to May 16th under ecological conditions prevailing in the San Joaquin Valley of Central California.

1 Drawing Sheet

BACKGROUND OF THE NEW VARIETY

The present invention relates to a new, novel and distinct variety of peach tree, *Prunus persica* which has been denominated varietally as 'Burpeachnineteen'.

The present variety of peach tree resulted from an ongoing program of fruit and nut tree breeding. The purpose of this program is to improve the commercial quality of deciduous fruit and nut varieties, and rootstocks, by creating and releasing promising selections of *prunus, malus* and *regia* species. To this end we make both controlled and hybrid cross pollinations each year in order to produce seedling populations from which improved progenies are evaluated and selected.

The seedling 'Burpeachnineteen' was originated by us from a population of seedlings grown in our experimental orchards located near Fowler, Calif. The seedlings, grown on their own roots, were the result from a controlled cross of the yellow-fleshed freestone peach tree 'P113-98' (nonpatented), which was used as the pollen parent, and an early ripening, white-fleshed, clingstone nectarine tree, of known parentage (unpatented), which was used as the seed parent. One seedling, which is the present variety, exhibited especially desirable characteristics, and was marked for subsequent observation. After the 1999 fruiting season, the new present variety was selected for advanced evaluation and repropagation.

ASEXUAL REPRODUCTION

Asexual reproduction of the new and distinct variety of peach tree was accomplished by budding the new peach tree to 'Nemaguard' Rootstock (not-patented). This was performed by us in our experimental orchard which is located near Fowler, Calif. Subsequent evaluations have shown those asexual reproductions run true to the original tree. All characteristics of the original tree, and its fruit, were established and appear to be transmitted through succeeding asexual propagations.

SUMMARY OF THE VARIETY

'Burpeachnineteen' is a new and distinct variety of peach tree, which is considered of large size, and which has vigorous growth. This new peach tree is also a regular and productive bearer of relatively large, firm, yellow fleshed, clingstone fruit, which have good flavor and eating qualities. This new tree has a medium chilling requirement of approximately 600 hours, and further produces relatively uniformly sized fruit throughout the tree. The fruit produced by this new variety has a non-melting flesh which makes it ideal for storage. In addition to the foregoing, the fruit of this new tree also appears to have good handling and shipping qualities. The 'Burpeachnineteen' peach tree bears fruit which are ripe for commercial harvesting and shipment on approximately May 8th to May 16$^{th}$. In relative comparison to the seed parent, the present new variety of peach tree bears fruit which ripen about 10 days earlier at the same geographical location.

BRIEF DESCRIPTION OF THE DRAWINGS

The accompanying drawing, which is provided, is a color photograph of the new variety of peach tree. The photograph depicts two whole mature fruit, and one mature fruit dissected substantially in the equatorial plane, and which reveals the flesh and the pit. Additionally the photograph displays a sample, vegetative shoot bearing typical leaves, and a stone with the flesh removed to reveal characteristic shape. The external coloration of the fruit, as shown, is sufficiently matured for harvesting and shipment. The colors in this photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society) and descriptions provided.

DETAILED DESCRIPTION

Referring more specifically to the pomological details of this new and distinct variety of peach tree, the following was observed in the fourth fruiting season under the ecological conditions prevailing at orchards located near the town of Fowler, county of Fresno, state of California. All major color code designations are by reference to The RHS Colour Chart (Fourth Edition) provided by The Royal Horticultural Society of Great Britain. Common color names are also occasionally used.

Tree:

*Size.*—Generally.—Considered medium to large as compared to other common commercial peach cultivars ripening in the early season of maturity. The tree of the present variety was pruned to a height of approximately 305.0 cm to about 315.0 cm at commercial maturity.

*Vigor.*—Considered moderately vigorous. The present peach tree variety grew from about 134.0 cm to 145.0 cm in height during the first growing season. The variety was pruned to a height of approximately 118.0 cm in the first dormant season, and primary scaffolds were selected for the desired tree structure.

*Productivity.*—Productive. Fruit set varies from 1.5 to several times more than the desired crop load. The fruit set is spaced by thinning to develop the remaining fruit into the desired market sized fruit. The number of the fruit varies with the prevailing climatic conditions and cultural practices employed during the bloom period, and is therefore not distinctive of this variety.

*Bearer.*—Regular. Fruit set has been heavy during the years of observation and thinning was necessary during the past 5 years.

*Form.*—Upright, and pruned to a vase shape.

*Density.*—Medium dense. It has been discovered that pruning the branches from the center of the tree to obtain a resulting vase shape allows for air movement and appropriate amounts of sunlight to enter the tree to enhance fruit color and renewal of fruiting wood throughout the tree.

*Hardiness.*—The present tree was grown and evaluated in USDA Hardiness Zone 9. Winter chilling requirements of the new tree are approximately 600 hours below 7.0 degrees C. The variety appears to be hardy under typical central San Joaquin Valley conditions.

Trunk:

*Diameter.*—Approximately 12.5 cm in diameter when measured at a distance of approximately 15.24 cm above the soil level. This measurement was taken at the end of the fourth growing season.

*Bark texture.*—Considered moderately rough, with numerous folds of papery scarfskin being present.

*Lenticels.*—Numerous flat, oval lenticels are present. The lenticels range in size from approximately 3.0 to about 6.0 millimeters in width; and from about 1.0 to about 2.0 millimeters in height.

*Lenticel color.*—Considered an orange brown, (RHS Greyed-Orange Group 172 B).

*Bark coloration.*—Variable, but it is generally considered to be a purple color, (RHS Greyed-Purple Group N187 A).

Branches:

*Size.*—Considered medium for the variety.

*Diameter.*—Average as compared to other peach varieties. The branches have a diameter of about 5.7 centimeters when measured during the fourth year after grafting.

*Surface texture.*—Average, and appearing furrowed on wood which is several years old.

*Crotch angles.*—Primary branches are considered variable between about 47 to 54 degrees from the horizontal axis. This characteristic is not considered distinctive of the variety, however.

*Current season shoots.*—Surface texture — Substantially glabrous.

*Internode length.*—Approximately 2.5 to about 2.7 cm.

*Color of mature branches.*—Medium brown, (RHS Brown Group 200 C).

*Current seasons shoots.*—Color.—Light green, (RHS Yellow-Green Group 144 B). The color of new shoot tips is considered a bright and shiny green (RHS Yellow-Green Group 144 A).

Leaves:

*Size.*—Considered medium-large for the species. Leaf measurements have been taken from vigorous, upright, current-season growth at approximately mid-shoot.

*Leaf length.*—Approximately 145.0 to about 152.0 millimeters.

*Leaf width.*—Approximately 34.0 to about 38.0 millimeters.

*Leaf base shape.*—Slightly oblique relative to the leaf longitudinal axis.

*Leaf form.*—Lancelolate.

*Leaf tip form.*—Acuminate.

*Leaf color.*—Upper Surface—Dark green, (approximately RHS Green Group 139 A).

*Leaf texture.*—Glabrous.

*Leaf color.*—Lower Surface.—Medium green, (RHS Green Group 137 A).

*Leaf venation.*—Pinnately veined.

*Mid-vein.*—Color.—Light yellow green, (RHS Yellow-Green Group 145 B).

*Leaf margins.*—Slightly undulating.

*Form.*—Considered crenate. Occasionally doubly so.

*Uniformity.*—Considered generally uniform.

*Leaf petioles.*—Size.—Considered medium. Length.—About 9.0 to about 12.0 mm. Diameter.—About 1.5 to about 2.0 mm. Color.—Pale green, (RHS Yellow-Green 144 A).

*Leaf glands.*—Size.—Considered medium. Approximately 1.5 mm in length and 1.0 mm in height. Number.—Generally one gland per margin side. Occasionally two glands per margin side. Type.—Reniform. Color.—Considered a pale orange brown, (RHS Orange-Red Group 31B).

*Leaf stipules.*—Size.—Medium large for variety. Number.—Typically 2 per leaf bud and up to 6 per shoot tip. Form — Lanceolate in form and having a serrated margin. Color.—Green, (RHS Green Group 137 B) when young but graduating to a brown color, (RHS Greyed-Orange group 166 A) with advancing senescence. The stipules are considered to be early deciduous.

Flower:

*Flower buds.*—Generally — The floral buds, depending upon the stage of development, are approximately 8.0 millimeters wide; about 12.0 millimeters long; conic in form; and slightly appressed relative to the bearing shoot.

*Flower buds.*—Color — This is dependent on the proximity to the bloom. The bud scales are reddish-brown, (approximately RHS Greyed-Purple Group 183 C). The buds are considered hardy typical central San Joaquin Valley climatic conditions.

*Hardiness.*—No winter injury has been noted during the last several years of evaluation in the central San Joaquin Valley. The current variety has not, however; been intentionally subjected to drought or heat stress, and therefore this information is not available.

*Date of first bloom.*—Feb. 27, 2003.

*Blooming time.*—Considered mid-season in comparison to other commercial peach cultivars grown in the central San Joaquin Valley. Date of full bloom was observed on Mar. 5, 2003. The date of bloom varies slightly with the prevailing climatic conditions and cultural practices.

*Duration of bloom.*—Approximately 9 days. This characteristic varies slightly with climatic conditions.

*Flower type.*—The variety is considered to have a showy type flower.

*Flower size.*—Flower diameter at full bloom is approximately 43.0 to about 48.0 millimeters.

*Bloom quantity.*—Considered abundant.

*Flower bud frequency.*—Normally 1 to 2 flower buds appear per node.

*Petal size.*—Generally — Considered large for the species. Length.—Approximately 18.0 to about 23.0 millimeters. Width.—Approximately 17.0 to about 19.0 millimeters.

*Petal form.*—Slightly ovoid.

*Petal count.*—Nearly always 5.

*Petal texture.*—Glabrous.

*Petal color.*—Light pink, (RHS Red-Purple Group 62 B) and darkening to a medium pink, (RHS Red-Purple Group N66 D).

*Fragrance.*—Slight.

*Petal claw.*—Form.—The claw is considered generally rotund and has a medium size when compared to other varieties. Length.—Approximately 10.0 to about 12.0 millimeters. Width.—Approximately 9.0 to about 11.0 millimeters.

*Petal margins.*—Generally considered variable, from nearly smooth to moderately undulate.

*Petal apex.*—Generally — The petal apices generally appear slightly grooved at the tip.

*Flower pedicel.*—Length.—Considered medium-long, and having an average length of approximately 4.0 to about 5.0 millimeters. Diameter.—Considered average, approximately 2.0 millimeters. Color.—A medium brown, (RHS Greyed-Orange Group 166 C).

*Floral nectaries.*—Color.—A dull orange, (RHS Greyed-Orange Group N167 B).

*Calyx.*—Surface Texture.—Generally glabrous. Color.—A dull red, (approximately RHS Greyed-Purple Group 183 A).

*Sepals.*—Surface Texture.—The surface has a short, fine pubescent texture. Size.—Average, and ovate in form. Color.—A dull red, (approximately RHS Greyed-Purple Group 184 C).

*Anthers.*—Generally.—Average in length. Color.—Red to reddish-orange dorsally, (approximately RHS Greyed-Red Group 178 A).

*Pollen production.*—Pollen is abundant, and has a yellow color, approximately RHS Yellow Orange Group 16 A).

*Filaments.*—Size.—Variable in length, considered medium short. Approximately 14.0 to about 17.0 millimeters in length. Color.—Considered white to a pinkish-white, (RHS Red Group 56 C).

*Pistil.*—Number.—Usually 1, rarely 2. Generally.—Average in size. Length.—Approximately 17.0 to 20.0 millimeters including the ovary. Color.—Considered a very pale green, (approximately RHS Yellow-Green Group 150 C). Surface Texture.—The variety has a long pubescent pistil.

Fruit:

*Maturity when described.*—Firm ripe condition (shipping ripe). Date of first picking.—May 8th, 2003. Date of last picking.—May 16, 2003. The date of harvest varies slightly with prevailing climatic conditions.

*Size.*—Generally — Considered medium large, and uniform.

*Average cheek diameter.*—Approximately 70.0 to about 78.0 millimeters.

*Average axial diameter.*—Approximately 66.0 to about 71.0 millimeters.

*Typical weight.*—Approximately 256.0 grams. This characteristic is highly dependent upon the prevailing cultural practices, and therefore not particularly distinctive of the variety.

*Fruit form.*—Generally — Considerably oblate. The fruit is generally uniform in symmetry.

*Fruit suture.*—Very shallow and smooth, extending from the base to apex. No apparent callousing or stitching exists along the suture line.

*Suture.*—Color — This has a yellow background color, (approximately RHS Yellow-Orange Group 14 B).

*Ventral surface.*—Form — Rarely indented.

*Apex.*—Rounded.

*Base.*—Generally a slightly indented base.

*Stem cavity.*—Generally considered round and uniform. Average depth of the stem cavity is about 7.0 mm. Average width is about 15 mm.

*Fruit skin.*—Thickness.—Considered medium in thickness, and tenacious to the flesh. Texture.—Short, fine and pubescent. The pubescence is moderately abundant. Taste.—Non-astringent. Tendency to crack.—None observed.

*Color.*—Blush Color.—This blush color is generally a deep red striping on a majority of the skin of the fruit (approximately RHS Red Group 46 A) and generally is more present on the basal portions of the fruit. The blush covers approximately 80–90% of the fruit skin surface. The percentage of blush on the fruit skin surface can vary, and is generally dependent to some degree upon the conditions under which the fruit was grown. Ground Color.—Yellow orange, (approximately RHS Yellow-Orange Group 14 B).

*Fruit stem.*—Medium in length, approximately 5.0 to about 7.0 millimeters. Diameter.—Approximately 2.0 millimeters. Color.—Pale yellow-green, (approximately RHS Yellow-Green Group N144 B).

*Flesh.*—Ripens.—Evenly. Texture.—Firm, juicy and dense. Considered non-melting. Fibers.—Few, small, and tender ones are found. Aroma.—Very slight. Eating Quality.—Very good. Flavor.—Considered sweet and mildly acidic. The flavor is considered both pleasant and balanced. Juice.—Moderate. Brix.—About 14.0 degrees. This characteristic varies slightly with the number of fruit per tree; prevailing cultural practices; and the surrounding climatic conditions. Flesh Color.—Pale yellow, (approximately RHS Yellow-Orange Group 18 A).

Stone:

*Type.*—Clingstone.

*Size.*—Considered medium for the variety. The stone size varies significantly depending upon the tree vigor, crop load and current growing conditions.

*Length.*—Average, about 22.0 to about 27.0 millimeters.

*Width.*—Average, about 19.0 to about 21.0 millimeters.

*Diameter.*—Average, about 14.0 to about 18.0 millimeters.

*Form.*—Ovoid.

*Base.*—The stone is slightly extended, and considered slightly oblique relative to the dorsal side.

*Apex.*—Shape.—The stone apex is raised and is generally without a prominent tip.

*Stone surface.*—Surface Texture — Irregularly furrowed toward the basal end. Pitting is abundant, generally, but is typically more noted on the basal end and also toward the dorsal edge. Ridges.—The surface texture is generally characterized by more prominant ridges along the ventral edges. Ventral Edge.—Width — Considered medium, and having a dimension of approximately 3.0 to about 4.0 millimeters at the mid-surface. Dorsal Edge.—Shape.—Irregular, lightly grooved, and having a reasonably jagged margin.

*Stone color.*—The color of the dry stone is generally considered a pale tan. (approximately Orange Group RHS 26 D).

*Tendency to split.*—Splitting has rarely been noted.

*Kernel.*—Size.—Kernel is considered medium. Form.—Considered ovoid. Pellicle.—Pubescent. Color.—(RHS Greyed-Orange Group 164 D). The kernel and its pellicle are usually considered immature because the subject variety ripens prior to the normal seed development period.

*Use.*—The subject variety 'Burpeachnineteen' is considered to be a Peach tree of the early season maturity, and which produces fruit which are considered firm, attractively colored, and which are useful for both local and long distance shipping.

*Keeping quality.*—Excellent. Fruit has stored well up to 25 days after harvest at 1.0 degree Celsius.

*Shipping quality.*—Good. The fruit of this new peach tree variety showed minimal bruising of the flesh or skin damage after being subjected to normal harvest and packing procedures.

*Resistance to insects and disease.*—No particular susceptibilities were noted. The present variety has not been tested to expose or detect any susceptibilities or resistances to any known plant and/or fruit diseases.

Although the new variety of peach tree possesses the described characteristics when grown under the ecological conditions prevailing near Fowler, Calif. in the central part of the San Joaquin Valley of California, it should be understood that variations of the usual magnitude and characteristics incident to changes in growing conditions, fertilization, pruning, pest control and horticultural management are to be expected.

We claim: Having thus described and illustrated our new variety peach tree, what we claim is new and desire to secure by Plant Letters Patent is:

1. A new distinct variety of peach tree substantially as illustrated and described, and which is characterized principally as to novelty by producing an attractively colored yellow-fleshed, clingstone peach which is mature for harvesting approximately May 8 to May 16 under the ecological conditions prevailing in the San Joaquin Valley of Central California.

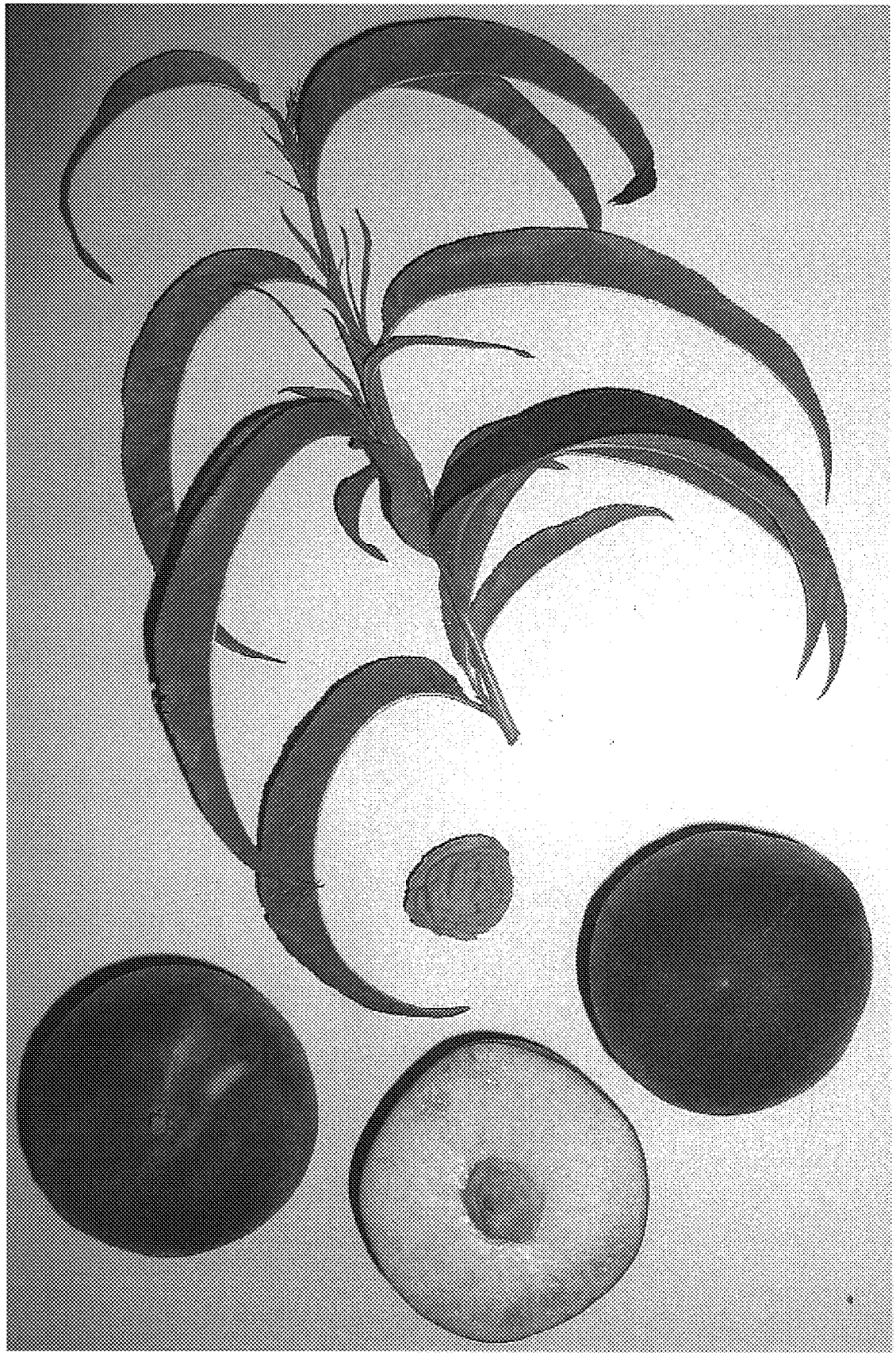

* * * * *